United States Patent [19]

Mann

[11] Patent Number: 5,383,911
[45] Date of Patent: Jan. 24, 1995

[54] RATE-RESPONSIVE PACEMAKER HAVING SELECTABLE RESPONSE TO ARM MOVEMENT AND PEDAL IMPACTS

[75] Inventor: Brian M. Mann, Beverly Hills, Calif.

[73] Assignee: Siemens Pacesetter, Inc., Sylmar, Calif.

[21] Appl. No.: 10,916

[22] Filed: Jan. 29, 1993

[51] Int. Cl.⁶ .......................................... A61N 1/368
[52] U.S. Cl. .................................... 607/19; 607/17
[58] Field of Search ................ 607/18, 19, 20, 22, 607/23, 24, 25, 26

[56] References Cited

U.S. PATENT DOCUMENTS

| | | | |
|---|---|---|---|
| 5,003,976 | 4/1991 | Alt | 607/20 |
| 5,063,927 | 11/1991 | Webb et al. | 607/19 |
| 5,137,019 | 8/1992 | Pederson et al. | 607/20 |

Primary Examiner—William E. Kamm
Assistant Examiner—Scott M. Getzow
Attorney, Agent, or Firm—Lisa P. Weinberg; Leslie S. Miller

[57] ABSTRACT

A rate-responsive pacemaker (10) generates stimulation pulses on demand at a rate determined by a sensor indicated rate (SIR) signal. The pacemaker includes, in a preferred embodiment, an activity sensor (26) that generates a raw sensor signal (27) as a function of sensed body motion. The raw sensor signal is processed by two parallel signal processing channels with each channel emphasizing a different aspect of the raw sensor signal. A first sensor processing channel (28) produces a first processed sensor signal ($S_A$) that is more sensitive to arm motion than to pedal impacts. A second sensor processing channel (30) produces a second processed sensor signal ($S_B$) that is more sensitive to pedal impacts than to arm motion. The first and second processed sensor signals are each weighted by a programmable amount, and are then combined to form the SIR signal.

21 Claims, 4 Drawing Sheets

RATE-RESPONSIVE PACEMAKER HAVING SELECTABLE RESPONSE TO ARM MOVEMENT AND PEDAL IMPACTS

BACKGROUND OF THE INVENTION

Field of the Invention

The present invention relates to implantable medical devices and methods, and more particularly, to an implantable rate-responsive pacemaker that generates stimulation pulses on demand at a rate determined by a sensor indicated rate (SIR) signal, where the SIR signal has a selectable response to various types of patient activity.

A pacemaker is a medical device that generates and delivers stimulation pulses to a patient's heart in order to cause the heart to beat in accordance with a prescribed sequence and pattern. Usually, the prescribed sequence and pattern is simply a prescribed pacing rate, with the pacemaker providing stimulation pulses only when the patient's heart fails to naturally beat on its own at a rate that is at least as fast as the prescribed pacing rate. Thus, if the pacemaker fails to naturally beat within a prescribed time interval (usually referred to as the "escape interval"), which prescribed time interval represents the period of the pacing rate, then and only then does the pacemaker step in with a pacemaker-generated stimulation pulse in order to force a heartbeat. In this manner, pacemaker-generated stimulation pulses are provided by the pacemaker only when needed, i.e., "on demand," when the heart is unable to beat on its own.

Most modern pacemakers are programmable, meaning that various parameters associated with the operation of the pacemaker may be noninvasively selected ("programmed") after the pacemaker has been implanted. Such programming is achieved through the use of an appropriate external programming device and telemetry circuit that establishes a suitable communication link with the memory circuits of the pacemaker. Examples of programmable, implantable pacemakers may be found, e.g., in U.S. Pat. Nos. 4,223,679 and 4,686,988; and in Furman, et al., A Practice of Cardiac Pacing, (Futura Publishing Co., Mount Kisco, N.Y.—1986).

In recent years, many pacemakers have also included rate-responsive pacing capabilities, meaning that the pacing rate is automatically adjusted as a function of some sensed physiologic-related parameter. Thus, such pacemakers include one or more sensors adapted to sense an appropriate physiologic-related parameter, such as physical activity, respiration rate, blood oxygen saturation, blood pH, blood temperature, or the like (any or all of which may provide some indication was to what the patient's heart rate should be), and appropriate signal processing circuitry for converting the sensed physiologic-related parameter to an appropriate control signal that controls the pacing rate. A pacemaker having such rate-responsive capability is referred to as a "rate-responsive pacemaker," and the control signal that controls the pacing rate as a function of the sensed physiologic-related parameter(s) is usually referred to as the "sensor indicated rate" (SIR) signal.

There are many types of rate-responsive pacemakers known in the art. Some utilize a single sensor in deriving the SIR signal, as described, e.g., in U.S. Pat. Nos. 4,140,132; 4,202,339; 4,428,378; 4,576,183; and 4,940,052. Others use multiple sensors, as taught, e.g., in U.S. Pat. Nos. 4,722,342; 4,782,836; and 5,097,831. Whether one or multiple sensors are used, there is a need to process the signal(s) generated by the sensor(s), which signal(s) is typically referred to as the "raw sensor signal," in an appropriate manner so that an SIR signal results that is truly indicative of a beneficial pacing rate.

The manner in which the raw sensor signal is processed can have a great effect upon the sensitivity of the SIR signal. Rate-responsive pacemakers that utilize the type of activity sensor and signal processing described in U.S. Pat. No. 4,428,378, for example, tend to produce an SIR signal that is overwhelmingly responsive to pedal impacts (walking signals) and relatively unresponsive to arm movements. This is apparently because, as described in the '378 patent, the raw sensor signal is filtered and peak amplitudes above a certain threshold level are averaged. Thus, as each step is taken, the sudden jolt or impact caused by the foot striking the ground tends to be more dominant in the processed sensor signal than are the somewhat less sudden and smoother portions of the raw sensor signal caused by arm movement. Disadvantageously, an SIR signal that is dominated by the pedal impact portions of the raw sensor signal may not always provide an indication of the most beneficial pacing rate. Thus, what is needed is a rate-responsive pacemaker wherein the dominance of sensed pedal impacts in determining the SIR signal may be selectively controlled.

In contrast, rate-responsive pacemakers that utilize the type of activity sensor and signal processing described in U.S. Pat. Nos. 4,940,053 or 5,040,535, tend to produce an SIR signal that is overwhelmingly responsive to arm movement of the arm on the side of the patient where the pacemaker is implanted. The raw sensor signal is processed in these patents to produce an SIR signal that is based on the energy content of the raw sensor signal or the average area of the raw sensor signal. Unfortunately, an SIR signal that is heavily dependent on arm motion, particularly arm motion of only one arm, may also not represent the most beneficial pacing rate. Hence, what is needed is a rate-responsive pacemaker wherein the SIR signal is not dominated by arm motion, particularly arm motion of just one arm.

In view of the above, it is thus evident that what is needed is a rate-responsive pacemaker wherein the raw sensor signal can be suitably processed to emphasize a selected aspect thereof, with the results of such processing thereafter being appropriately weighted in the formation of the SIR signal, thereby selectively controlling the sensitivity of the SIR signal to various sensed events, e.g., pedal impacts and/or arm motion.

SUMMARY OF THE INVENTION

Accordingly, it is a general feature of the invention to provide a rate-responsive pacemaker wherein the aforementioned problems are eliminated and the aforementioned needs are met.

More specifically, it is a feature of the invention to provide a rate-responsive pacemaker using an activity sensor wherein the dominance of sensed pedal impacts in determining the SIR signal may be selectively controlled, and wherein the SIR signal is not dominated by arm motion, particularly arm motion of just one arm.

It is a further feature of the invention to provide a rate-responsive pacemaker wherein the raw sensor signal can be suitably processed to emphasize a selected aspect or aspects thereof, with the results of such processing thereafter being appropriately weighted in the formation of the SIR signal. In this manner, the sensitivity of the resulting SIR signal to various sensed events, e.g., pedal impacts and/or arm motion, may be selectively controlled by appropriate weighting of the raw sensor signal processing results.

Like rate-responsive pacemakers of the prior art, the rate-responsive pacemaker of the present invention includes at least one sensor that generates a raw sensor signal as a function of a sensed physiologic-related parameter, e.g., body motion. Further, like rate-responsive pacemakers of the prior art, the raw sensor signal is processed in order to determine a sensor indicated rate (SIR) signal. The SIR signal is then used by the pacemaker in conventional manner to set the pacing rate at which the pacemaker provides stimulation pulses on demand, or as otherwise programmed.

Unlike rate-responsive pacemakers of the prior art, however, the rate-responsive pacemaker of the present invention includes parallel and independent sensor signal processing channels wherein the raw sensor signal is processed, with the results from each independent channel being weighted by an appropriate amount (the "weighting factor") in order to form the final SIR signal. Each sensor signal processing channel is configured to emphasize a different aspect of the raw sensor signal. A first sensor signal processing channel thus produces a first processed sensor signal that is more sensitive to a first type of sensed physiologic-related activity than to other types of physiologic-related activities. For example, the first sensor signal processing channel may generate a first processed sensor signal that is more sensitive to arm motion than to pedal impacts. Similarly, a second sensor signal processing channel produces a second processed sensor signal that is more sensitive to a second type of physiologic-related activity than to the first or other types of physiologic-related activities. For example, the second sensor signal processing channel may generate a second processed sensor signal that is more sensitive to pedal impacts than to arm motion. Other sensor signal processing channels may also be employed, as required, to produce additional processed sensor signals that are respectively more sensitive to a given type of physiologic-related activity than to other physiologic-related activities. The first, second, and any other, processed sensor signals from the respective sensor signal processing channels are then each weighted by the appropriate weighting factor, and all of the weighted processed sensor signals are then combined to form the SIR signal used by the rate-responsive pacemaker.

In accordance with one aspect of the invention, the weighting factor for each sensor signal processing channel (or the relative ratio of weighting factors used in the plural sensor signal processing channels) is a programmable parameter that may be set by appropriate medical personnel at the time of implant, and noninvasively changed thereafter as often as necessary.

In accordance with another aspect of the invention, the weighting factor that defines the makeup of the SIR signal may itself be a variable or function that automatically changes with time and/or other sensed parameters.

In accordance with one embodiment, the present invention may be characterized as an implantable rate-responsive pacemaker that is selectively responsive to different types of body motion, and more particularly where pedal impacts are weighted differently than arm motion in determining the overall body motion to which the pacemaker responds. Such pacemaker includes: (1) rate-responsive pacing means for generating stimulation pulses on demand at a rate determined by a sensor indicated rate (SIR) signal; (2) a body motion sensor that generates a raw sensor signal as a function of sensed body motion; (3) a first sensor processing channel that processes the raw sensor signal so as to generate a first processed sensor signal that is more sensitive to arm motion of the patient than to pedal impacts of the patient; (4) a second sensor processing channel that processes the raw sensor signal to generate a second processed sensor signal that is more sensitive to pedal impacts of the patient than to arm motion of the patient; and (5) weighting means for combining the first and second processed sensor signals to form the SIR signal as a function of a prescribed weighting signal. Advantageously, the weighting signal need not be a fixed amount, but may be a selectable or programmable amount. Thus, the amount of weight given each of the first and second processed sensor signals in the formation of the SIR signal may be a selectable or programmable amount.

More generally, the present invention may be characterized as an implantable rate-responsive pacemaker that includes: (1) a sensor for sensing a physiological parameter indicative of a desired heart rate; (2) first sensor signal generating means responsive to the physiological parameter sensed by the sensor for generating a first sensor signal in accordance with a first sensor processing scheme; (3) second sensor signal generating means responsive to the physiological parameter sensed by the sensor for generating a second sensor signal in accordance with a second sensor processing scheme; (4) processing means for generating a sensor indicated rate (SIR) signal as a specified combination of the first and second sensor signals; and (5) pacing means for providing stimulation pulses on demand at a rate determined by the SIR signal. Such pacemaker thus advantageously utilizes the sensed physiological parameter to control the rate at which the pacing means provides stimulation pulses on demand as a specified combination of the first and second sensor processing schemes.

Another way of characterizing the present invention is as an implantable rate-responsive pacemaker that includes: (1) pulse generating means for generating stimulation pulses on demand at a rate determined by a sensor indicated rate (SIR) signal; (2) a sensor that generates a raw sensor signal as a function of a sensed physiologic-related parameter; (3) sensor processing means for processing the raw sensor signal in accordance with a plurality of sensor signal processing schemes, with each of the sensor signal processing schemes generating a respective plurality of processed sensor signals, and with each of the processed sensor signals being more sensitive to a particular aspect of the raw sensor signal than are the other processed sensor signals; and (4) SIR signal generating means for combining the plurality of processed sensor signals to form the SIR signal in accordance with a prescribed function. The pulse generating means of such a pacemaker thus generates the stimulation pulses on demand at a rate determined by the raw sensor signal and the prescribed function, which prescribed function may be programmed to define a desired combination of the particular aspects of the raw sensor signal to which each of the processed sensor signals is more sensitive.

Still further, the present invention may be viewed as a method of operating a rate-responsive pacemaker that includes a sensor that generates a raw sensor signal as a function of a sensed physiologic-related parameter. The method includes: (a) processing the raw sensor signal in accordance with a first signal processing scheme to produce a first processed sensor signal, with the first signal processing scheme being adapted to emphasize a first particular aspect of the raw sensor signal; (b) processing the raw sensor signal in accordance with a second signal processing scheme to produce a second processed sensor signal, with the second signal processing scheme being adapted to emphasize a second particular aspect of the raw sensor signal; (c) combining the first and second processed sensor signals in accordance with a selected weighting criteria to produce a sensor indicated rate (SIR) signal; and (d) generating stimulation pulses on demand at a rate determined by the SIR signal.

BRIEF DESCRIPTION OF THE DRAWINGS

The above and other aspects, features and advantages of the present invention will be more apparent from the Detailed Description of the Invention presented in conjunction with the following drawings, wherein.

Corresponding reference characters indicate corresponding components throughout the several views of the drawings.

DETAILED DESCRIPTION OF THE INVENTION

Figure 1:
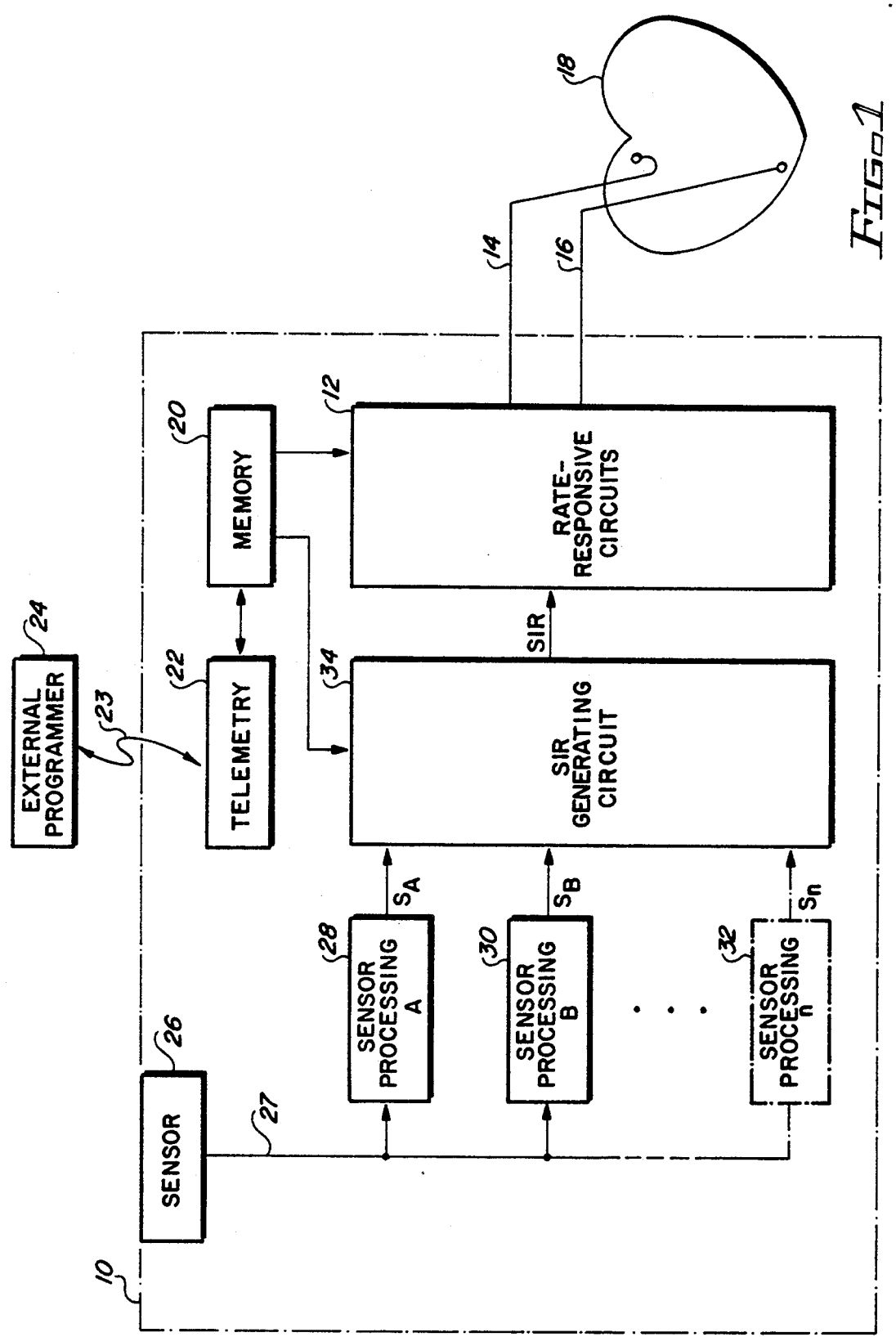
FIG. 1 shows a functional block diagram of a rate-responsive pacemaker made in accordance with the present invention.

The following description is of the best mode presently contemplated for carrying out the invention. This description is not to be taken in a limiting sense, but is made merely for the purpose of describing the general principles of the invention. The scope of the invention should be determined with reference to the claims.

The following U.S. Patents and patent applications, all of which are hereby incorporated herein by reference, provide additional detail and background associated with the design and operation of various features of an implantable rate-responsive pacemaker, any or all of which could be incorporated into a rate-responsive pacemaker made in accordance with the present invention: U.S. Pat. Nos. 4,223,679; 4,428,378; 4,686,988; 4,712,555; 4,771,780; 4,809,697; 4,846,195; 4,847,617; 4,940,052; 4,940,053; and 5,040,535; and U.S. patent applications (all assigned to the same assignee as is the present application): Ser. No. 07/846,460, filed Mar. 2, 1992, entitled "Method for Recording and Reporting a Sequential Series of Pacing Events"; Ser. No. 07/844,818, filed Mar. 2, 1992, entitled "Method and System for Automatically Adjusting the Sensor Parameters of a Rate-Responsive Pacemaker"; and Ser. No. 07/844,807, filed Mar. 2, 1992, entitled "Rate-Responsive Pacemaker Having Automatic Sensor Threshold with Programmable Offset."

As indicated above, the present invention broadly relates to a particular type of rate-responsive pacemaker wherein a raw sensor signal, indicative of a particular type of sensed physiologic-related parameter, is independently processed in separate sensor signal processing channels. The results of such independent and separate processing are thereafter combined, using an appropriate weighting criteria, to formulate a sensor indicated rate (SIR) signal. The sensor indicated rate signal is thereafter used by the pacemaker to provide stimulation pulses at a rate determined by the SIR signal in accordance with a programmed mode of operation, e.g., on demand.

The manner in which the rate-responsive pacemaker of the invention provides stimulation pulses at the SIR rate may be conventional, e.g., as taught in any of the aforementioned patents that have been incorporated herein by reference, or any other rate-responsive pacing technique. Accordingly, the details associated with such rate-responsive pacing will not be repeated herein. All that matters for purposes of the present invention is that some rate-responsive pacing circuitry or means be provided for generating stimulation pulses on demand (or in accordance with some other programmed mode of operation) at a rate controlled by the SIR signal. The present invention, while including such rate-responsive circuitry or means, thus focuses primarily on the manner in which the SIR signal is generated.

Also, for purposes of the present invention, the manner in which the raw sensor signal is generated may be conventional. That is, the type of sensor(s) used to generate the raw sensor signal(s) may be of the same type as are known and used in the art. Thus, while a preferred sensor for use with a pacemaker made in accordance with the present invention is an activity sensor designed to sense body motion, it is to be understood that the invention, unless otherwise indicated, is not to be limited to an activity sensor. Any sensor, or combination of sensors, that generates a raw sensor signal indicative of a sensed physiologic-related parameter or parameters, whether such parameter(s) comprises patient motion, patient activity, blood temperature, blood oxygen saturation, blood pH level, polarization time interval, pre-ejection time interval, repolarization time interval, respiration rate, or the like, may be used with the present invention.

Referring to FIG. 1, a functional block diagram of a rate-responsive pacemaker 10 made in accordance with the present invention is shown. The pacemaker 10 includes a rate-responsive pacing circuit 12, which generates stimulation pulses that are delivered to a patient's heart 18 over pacing leads 14 and/or 16. While two pacing leads 14 and 16 are shown in FIG. 1, it is to be understood that such is only exemplary. Any number of pacing leads, from a single unipolar lead, to a multiplicity of multi-polar leads (e.g., bipolar leads), may be used with the pacemaker 10. As is known in the art, the pacing leads 14 and/or 16 may also be used to sense cardiac events, e.g., depolarization of the atrium (manifest by the occurrence of a P-wave) or depolarization of the ventricles (manifest by the occurrence of an R-wave).

A memory circuit 20 is coupled to the pacing circuit 12. Operating parameters associated with the operation of pacemaker, e.g., operating parameters that define a programmed mode of operation, are stored in the memory circuit 20. Similarly, data sensed by the pacing circuits, e.g., electrogram data that defines the occurrence of P-waves and/or R-waves, or status data that indicates the state of the pacing circuits 12, may be stored in the memory circuit 20.

The data stored in the memory circuit 20 may be programmably changed (uploaded), or examined (downloaded) from an external programmer 24. Such uploading and/or downloading is achieved through the use of a telemetry circuit 22 that forms part of the pacemaker 10. The telemetry circuit 22, when activated, allows a noninvasive communication link 23 to be established between the pacemaker 10, which may be implanted in the patient, and the external programmer 24. The design and operation of the telemetry circuit 22, the external programmer 24, the memory circuit 20, and the rate-responsive pacing circuits 12 may be conventional, as described, e.g., in the aforementioned U.S. Patents and copending U.S. patent applications. Typically, the operation of the pacing circuit 12 is programmed to provide stimulation pulses on demand to the heart 18 at a rate determined by a sensor indicated rate (SIR) signal.

Still referring to FIG. 1, it is seen that the pacemaker 10 also includes a physiological sensor 26, described more fully below, adapted to sense a physiologic-related parameter of the patient. The sensor 26 generates a raw sensor signal that is made available on signal line 27. (Hereafter, a signal that appears on a corresponding signal line may be referred to by the reference numeral of the signal line on which the signal appears, e.g., the "raw sensor signal 27.") The raw sensor signal is then processed in plural sensor signal processing channels 28, 30, . . . 32. That is, a first sensor signal processing channel 28, also labeled as "sensor processing A," processes the raw sensor signal 27 to produce a processed sensor signal $S_A$. Similarly, a second sensor signal processing channel 30, also labeled as "sensor processing B," processes the raw sensor signal 27 to produce a processed sensor signal $S_B$. Additional sensor signal processing channels are used, up to an $n^{th}$ sensor signal processing channel 32, shown in FIG. 1 as "sensor processing n," in order to further process the raw sensor signal, with each such additional sensor signal processing channel producing a respective processed sensor signal $S_n$.

The processing of the raw sensor signal 27 carried out by each of the respective sensor signal processing channels 28, 30, . . . 32, is carried out in parallel with and independent from the processing carried out by the other sensor signal processing channels. Further, the particular type of sensor signal processing carried out by each sensor signal processing channel is designed to emphasize a different aspect of the raw sensor signal 27. Thus, for example, sensor signal processing channel 28 may amplify, filter and average the low frequency components of the raw sensor signal 27; while sensor signal processing channel 30 may amplify, filter and average the high frequency components of the raw sensor signal 27. Alternatively, one sensor signal processing channel may average the peak amplitude components of the raw sensor signal 27 above a prescribed threshold level; while another sensor signal processing channel may integrate the raw sensor signal, and thus compute a processed sensor signal that represents the area, or energy, associated with the raw sensor signal. Still further, one sensor signal processing channel may compute the mean value of the raw sensor signal above a first threshold value, and another sensor signal processing may compute the average RMS value of the raw sensor signal above the first or a second threshold value. A further sensor signal processing channel may compute the slope of the raw sensor signal and generate a pulse if the slope exceeds a prescribed threshold value, with the pulses thereafter being counted or averaged. Indeed, there is no limit to the types of different processing that may be performed by the respective sensor signal processing channels in accordance with the present invention as the raw sensor signal 27 is processed and converted to an appropriate processed sensor signal.

After being parallel processed in the sensor signal processing channels 28, 30, . . . 32, and producing respective processed sensor signals $S_A$, $S_B$, . . . $S_n$, the processed sensor signals are combined in an SIR generating circuit 34. The manner in which such processed sensor signals are combined to produce the SIR signal is determined by a specified function defined by appropriate control parameters stored in the memory 20, or otherwise set within the SIR generating circuit 34. Typically, as described below, such specified function is simply a weighting function that defines respective weighting factors that define how much weight is to be given the processed sensor signal obtained from each sensor signal processing channel, e.g., 60% weight given to $S_A$, and 40% weight given to $S_B$. However, it is to be understood that the specified function is not limited to a simple weighting function, and that any suitable function that combines the processed sensor signals so as to produce a desired SIR signal, may be used with the present invention.

As an example of a more general function that may be used by the invention to produce the SIR signal from the respective processed sensor signals, consider the relationship:

$$SIR = k_1 f_1(t)(S_A) + k_2 f_2(t)(S_B) + \ldots + k_n f_n(t)(S_n).$$

In such general function, $k_i$ represents an appropriate scaling factor, $f_1(t)$ is a first function of time that defines when and how much weight is to be given to the processed signal $S_A$, $f_2(t)$ is a second function of time that defines when and how much weight is to be given to the processed signal $S_B$, and $f_n(t)$ is an $n^{th}$ function of time that defines when and how much weight is to be given the processed signal $S_n$. Using such general function, it is thus possible to control the SIR signal so that at a particular time, where "time" may be measured relative to real time, a cardiac cycle(s), and/or a cardiac rate (all of which can be measured and tracked in a conventional pacing circuit 12), a given processed sensor signal is weighted differently in the makeup of the SIR signal than it is at another time. For example, at the onset of an increased heart rate, the sensor signal $S_B$ may be weighted more heavily than it is after a prescribed time of increased heart rate; while the sensor signal $S_A$ may be weighted less heavily at the onset of the increased heart rate than it is after the prescribed time. Thus, it is seen that the present invention provides a great deal of versatility in how much the respective processed sensor signals contribute to the formation of the SIR signal, which SIR signal controls the rate at which the pacing circuit 12 provides stimulation pulses on demand.

Figure 2:
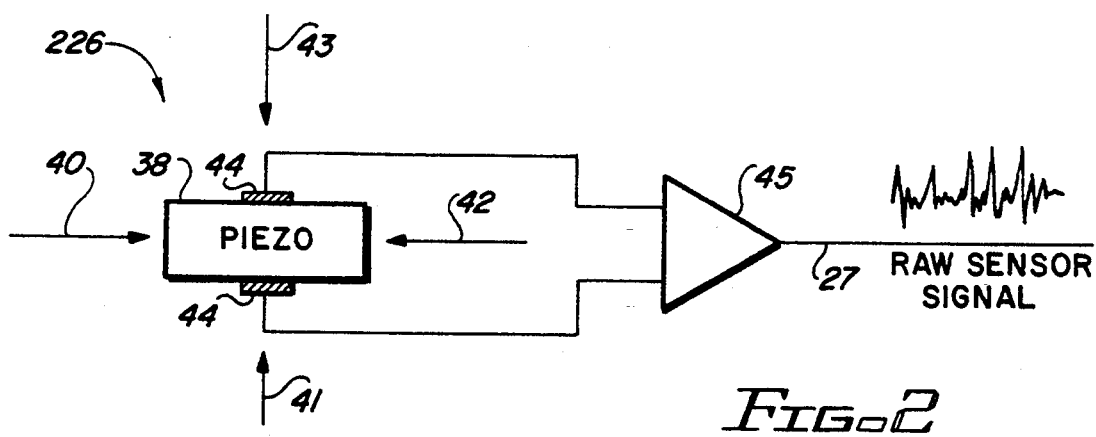
FIG. 2 diagrammatically illustrates an activity sensor made from a piezoelectric sensor.

A preferred type of physiological sensor 26 for use with the pacemaker 10 in accordance with the present invention is an activity sensor that senses the physical activity or motion of the patient. One type of such activity sensor is shown in FIG. 2 as the sensor 226. The sensor 226 comprises a piezoelectric element 38. When the piezo-element 38 is subjected to physical forces 40–43, an electrical signal is manifest on output terminals 44. Such electrical output signal may then be amplified by amplifier 45 in order to produce the raw sensor signal 27. Activity sensors of the type shown in FIG. 2 are used, e.g., in the pacemakers described in U.S. Pat. Nos. 4,140,132; 4,428,378; and 4,940,053.

Figure 3:
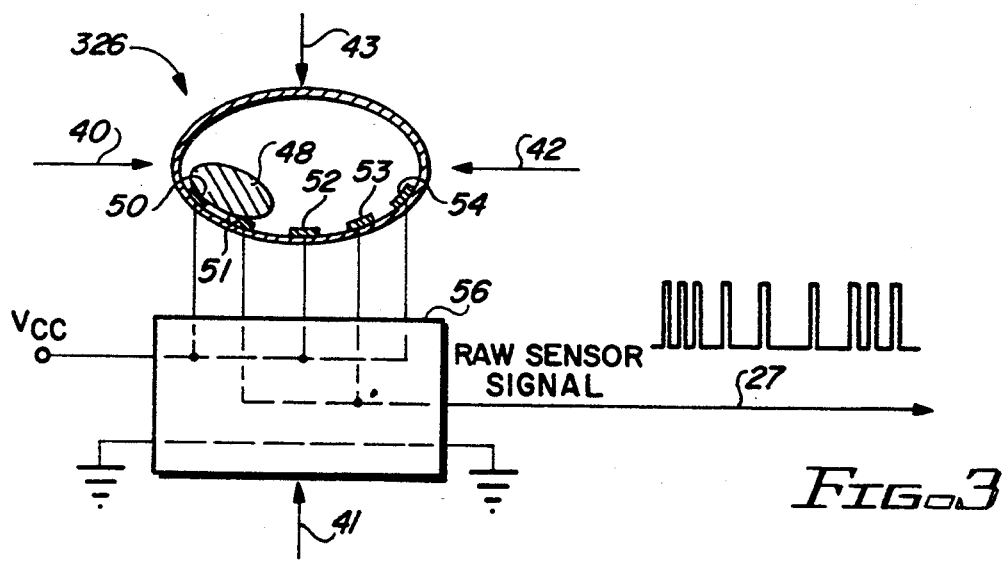
FIG. 3 diagrammatically illustrates an activity sensor that includes a movable conductive element that selectively makes and breaks electrical contact with a plurality of terminal contacts.

Another type of activity sensor is shown in FIG. 3 as the motion sensor 326. The motion sensor 326 includes a hollow closed element 46 wherein a conductive ball 48, made e.g. from a bead of mercury, is allowed to move as a function of external forces 40–43 to which the element 46 is subjected. Spaced-apart terminals 50–54 are positioned around the inside of the element 46 so that as the ball 48 moves around within the element 46 it always makes contact with at least two of the terminals 50–54. The terminals 50–54, in turn, are connected to a suitable voltage potential $V_{CC}$ through a connection circuit 56. The raw sensor signal 27, obtained from the connection circuit 56, thus comprises a series of pulses that are formed as the ball 48 makes and breaks electrical contact with the various terminals 50–54. Such pulses have a width and frequency that varies as a function of how rapidly the ball 48 moves around within the element 46, which in turn is determined by the external forces 40–53 to which the element is subjected. Motion sensors of the type shown in FIG. 3 are described in U.S. Pat. Nos. 4,771,780 and 4,846,195.

It is contemplated that an activity-based rate-responsive pacemaker 10 made in accordance with the present invention may use either an activity sensor as shown in FIG. 2 and/or a motion sensor as shown in FIG. 3, or any other type of suitable activity sensor. In accordance with a preferred embodiment of an activity-based rate-responsive pacemaker, however, a piezo-sensor 226 of the type shown in FIG. 2 is used. The raw sensor signal 27 generated by such sensor 226 is further processed in two sensor signal processing channels in accordance with two separate signal processing schemes.

A first signal processing scheme is carried out by the sensor signal processing channel 28 (FIG. 1), and determines the "energy content" of the raw sensor signal, as taught in U.S. Pat. No. 4,940,053, or by the average amplitude of the raw sensor signal above a prescribed threshold, as taught in U.S. Pat. No. 5,040,535. It has been determined that such signal processing tends to be more sensitive to arm motions of the patient, and particularly to arm motion of the patient on the same side of the patient where the pacemaker (and hence the sensor 226) is implanted. As a result, the processed sensor signal $S_A$ tends to be much more responsive to arm motion (and particularly to left or right arm motion, depending upon which side of the patient the pacemaker is implanted) than to other types of patient motion.

A second signal processing scheme is carried out by the sensor signal processing channel 30 (FIG. 1), and essentially determines the average peak value of the raw sensor signal above a certain threshold, as described in U.S. Pat. No. 4,428,378. It has also been determined that such signal processing is much more sensitive to pedal impacts (walking) of the patient than to other types of patient motion. Hence, the processed sensor signal $S_B$ tends to be much more responsive to pedal impacts than to other types of patient motion.

In accordance with the preferred embodiment of the present invention, the processed sensor signals $S_A$ and $S_B$ are combined into a single SIR signal using different ratios of the $S_A$ and $S_B$ signals. Moreover, the ratios or weighting factors used to define the make-up of the SIR signal are programmable. This means that a physician can program the pacemaker 10 to be relatively more responsive to arm motion (arm waving), or relatively more responsive to walking (pedal impacts). For example, the SIR signal may use 80% of the arm motion signal $S_A$, and 20% of the pedal impact signal, $S_B$, in formulating the SIR signal. In this manner, then, the present invention advantageously allows the physician to select between an SIR signal which is relatively more sensitive to pedal impacts at one extreme, or an SIR signal which is relatively more responsive to arm motion or waving at the other extreme, or any mix or combination between these two extremes.

Figure 4:
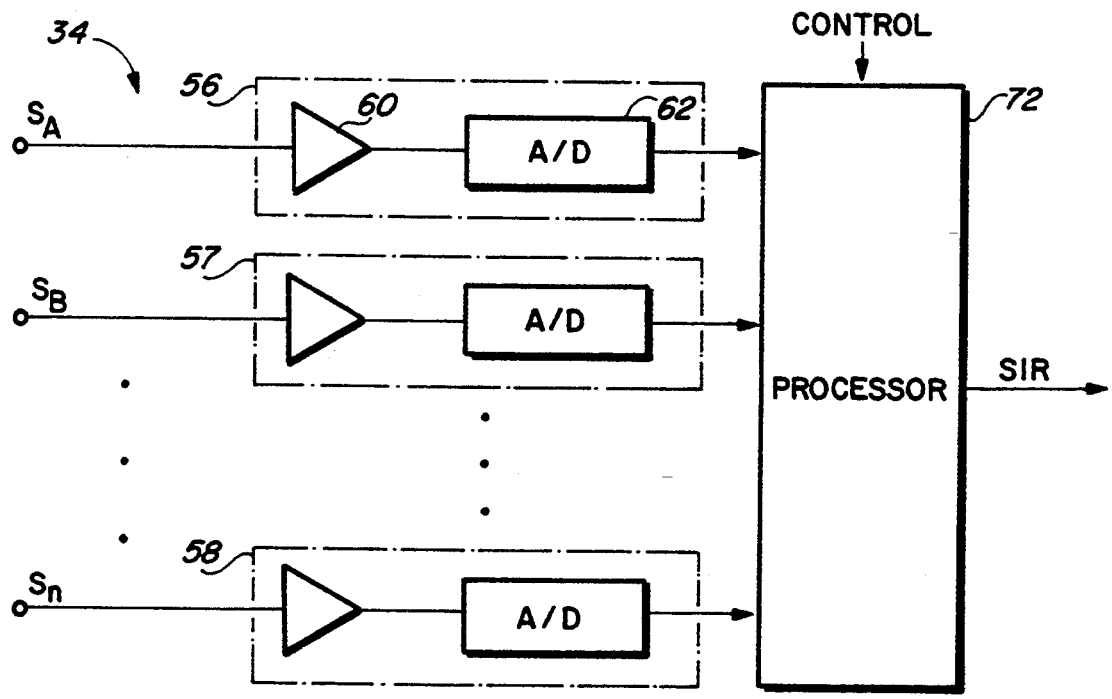
FIG. 4 is functional block diagram of the SIR generating circuit of FIG. 1.

Turning next to FIG. 4, a functional block diagram of the SIR generating circuit 34 of FIG. 1 is illustrated. As shown in FIG. 4, such circuit 34 includes separate input channels 56, 57, ... 58 for each of the processed sensor signals $S_A$, $S_B$, ... $S_n$ that are received from the respective sensor signal processing channels 28, 30, ... 32. Each input channel includes a buffer amplifier/limiter 60 and an analog-to-digital (A/D) converter 62. The buffer amplifier/limiter 60 amplifies the received processed sensor signal, as required, and limits it between defined maximum and minimum values. The resulting signal is then converted to a digital signal, $S_{DA}$, by the A/D converter 62. For example, the sensor processed signal $S_A$ may be amplified by the amplifier 60 so as to have a value of between 0 and 3 volts for the maximum signal swings of the processed sensor signal. Such signal is then converted by the A/D converter 62 to assume, e.g., one of thirty-two possible digital values, ranging between 0 and 31. A digital value of 0 is assumed for an $S_A$ signal having a minimum value, and a digital value of 31 is assumed for an $S_A$ signal having a maximum value.

In a similar manner, the input channel 57 converts the processed sensor signal $S_B$ into a digital signal $S_{DB}$ that assumes a value between specified maximum and minimum digital values. Likewise, any other input channels, such as the input channel 58, convert their respective processed sensor signal $S_n$ into a digital signal $S_{Dn}$ that assumes values between specified maximum and minimum digital values.

After preliminary processing in the respective input channels 56–58, the resulting processed sensor signals $S_{DA}$, $S_{DB}$, ... $S_{Dn}$, are presented to a suitable processor 72. The processor 72 combines the processed signals as controlled by a specified function in order to produce the SIR signal.

Figure 5:
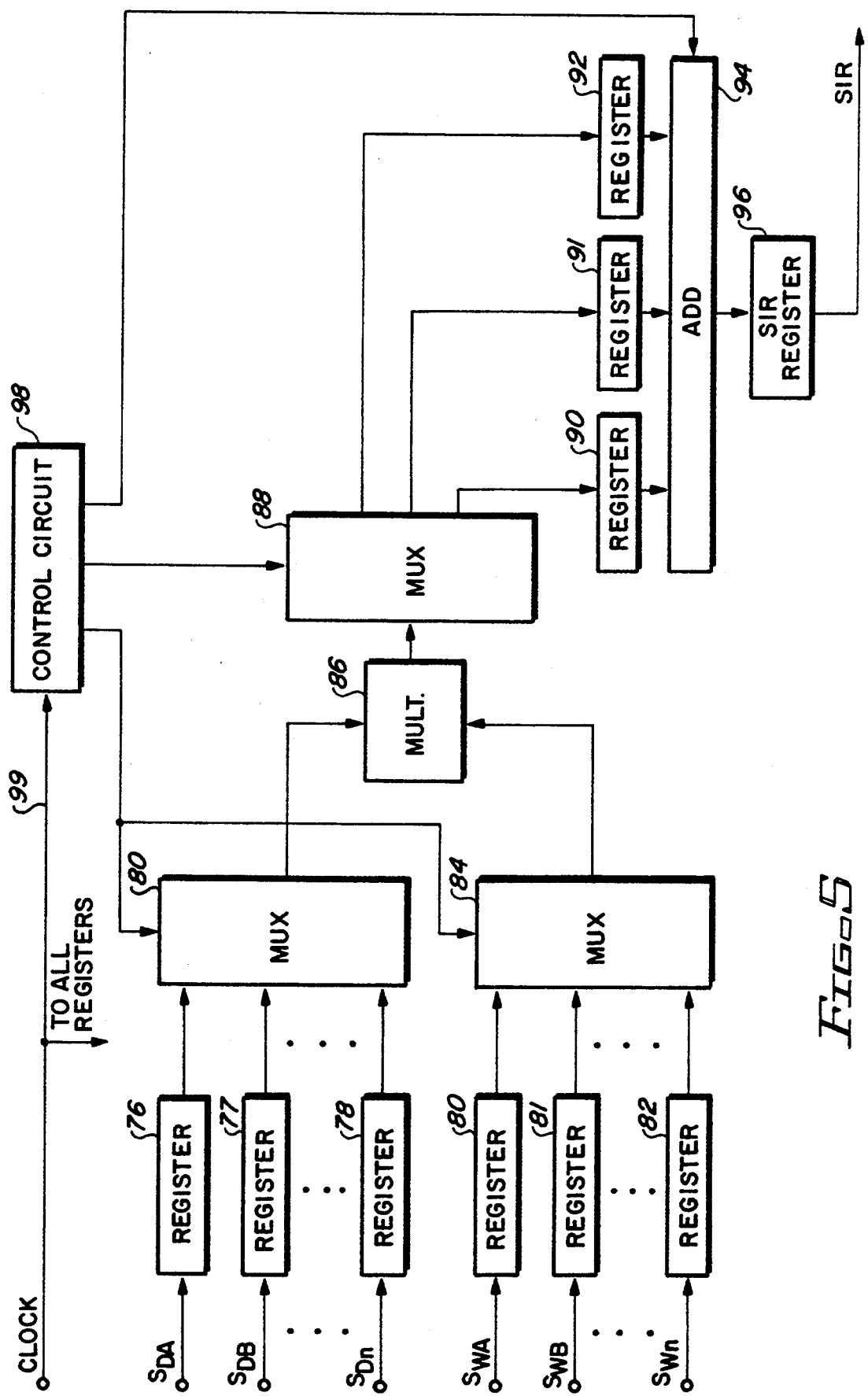
FIG. 5 shows a block diagram of one embodiment of a processing scheme used to weight the processed sensor signals by a selected weighting factor.

FIG. 5 shows a functional block diagram of one embodiment of the processor 72. It is to be emphasized that what is shown in FIG. 5, is functional. It is submitted that those of skill in the art may fashion appropriate circuitry to realize the functions shown in FIG. 5 using appropriate hardware, firmware, and/or software, as is known in the art.

As seen in FIG. 5, the converted digital signals $S_{DA}$, $S_{DB}$, ... $S_{Dn}$ are held in respective registers 76, 77, ... 78. At the same time, an appropriate weighting factor for each sensor signal processing channel, $S_{WA}$, $S_{WB}$, ... $S_{Wn}$, is retrieved and held in respective registers 80, 81, ... 82. At an appropriate time, as controlled by a control circuit 98 driven by a clock signal 99, a multiplexer circuit (MUX) 80 selects one of the converted vales held in the registers 76, 77, ... 78 and applies it to a multiplication circuit 86 as a multiplicand. At the same time, another MUX 84 selects an appropriate one of the weighting factors held in the registers 80, 81, ... 82 and also applies it to the multiplication circuit 86 as a multiplier. The multiplication circuit 86 then multiplies the multiplicand by the multiplier and applies the product, through another MUX circuit 88, to one of the holding registers 90, 91, ... 92. The products held in the holding registers 90, 91, ... 92 are then applied to the adding circuit 94, where they are summed (combined). The result of such summation is placed in an SIR register 96, the contents of which represent the value of the SIR signal.

Thus, as shown in FIG. 5, it is seen that the resulting SIR signal is effectively determined to be:

$$SIR = S_{WA}S_{DA} + S_{WB}S_{DB} + \ldots + S_{Wn}S_{Dn}.$$

For example, if at the time the computation of the SIR signal is made, $S_{DA}=20$, and $S_{DB}=16$, and if the weighting factors for the sensor signal A channel and the sensor signal B channel are programmed to be $S_{WA}=0.8$ and $S_{WB}=0.2$, then the SIR signal is $$SIR = 0.8 \times 20 + 0.2 \times 16 = 19.2.$$

Figure 6:
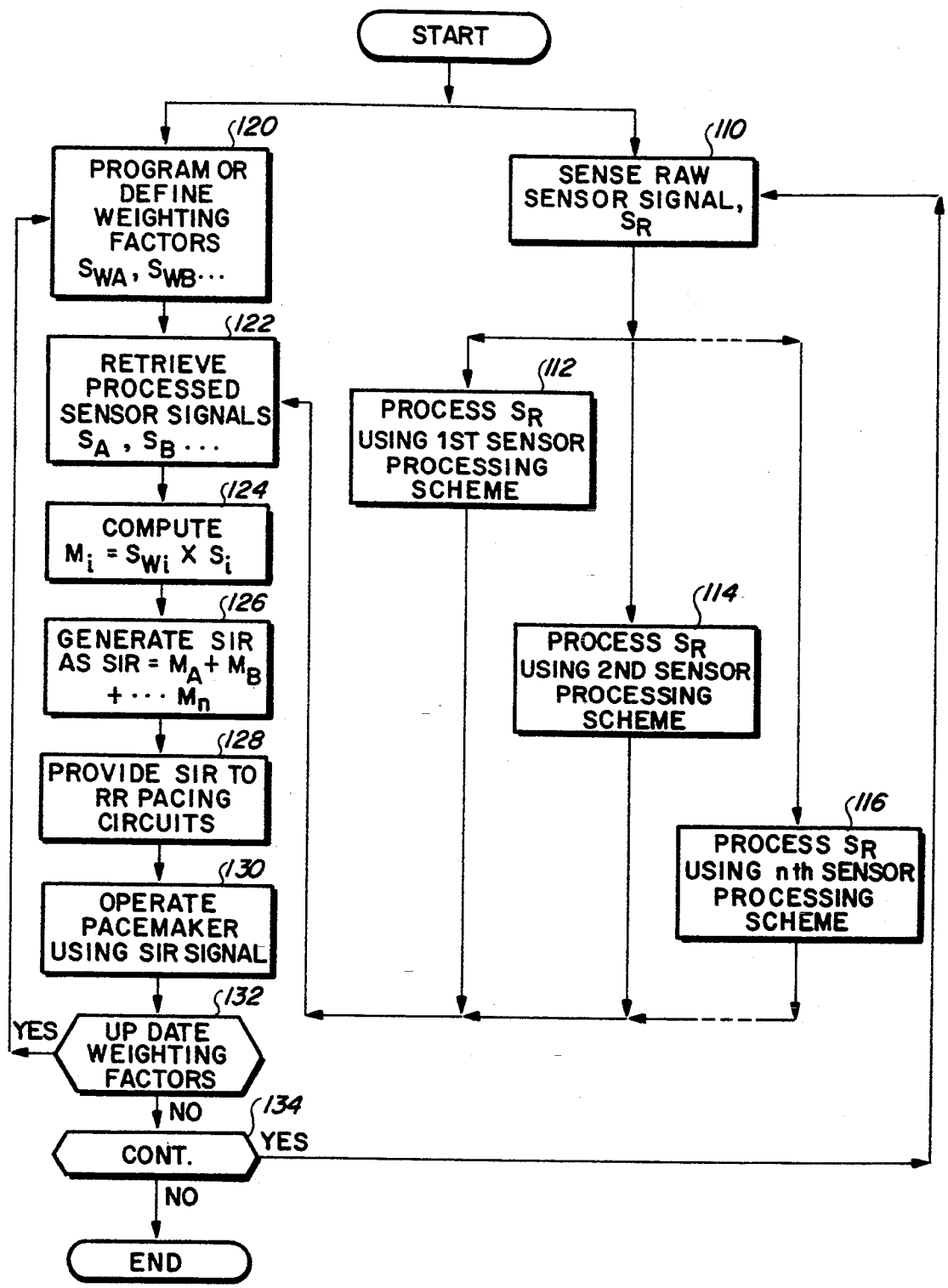
FIG. 6 shows a flowchart that illustrates the basic method used to operate a rate-responsive pacemaker in accordance with the present invention.

Turning next to FIG. 6, there is shown a flowchart that illustrates the basic method used to operate a rate-responsive pacemaker in accordance with the present invention. In such flowchart, each main step is represented by a separate "box" or "block," with each of the blocks having an appropriate reference numeral assigned thereto (for explanatory purposes), and with each of the blocks being joined with a directional line that illustrates the "flow" or sequence in which the steps are performed.

After the method is started, or at some point prior to invoking the method, the various weighting factors, $S_{WA}$, $S_{WB}$, ... $S_{Wn}$, that are assigned to each of the sensor signal processing channels are programmed or otherwise defined (block 120). As previously explained, in a simple application of the present invention, such weighting factors are a fixed percentage, or number. In more complex applications, however, the weighting factors may be more properly characterized as weighting functions, and each may independently vary as a function of time, elapsed cycles, heart rate, etc.

Independent of the setting of the weighting factors $S_{WA}$, $S_{WB}$, ... $S_{Wn}$, the raw sensor signal, $S_R$, is sensed (block 110) by the sensor 26 (FIG. 1). This raw sensor signal $S_R$ is then processed independently in each of the sensor signal processing channels. Stated another way, the raw sensor signal $S_R$ is processed in accordance with a first processing scheme in order to produce the processed sensor signal $S_A$ (block 112). The raw sensor signal $S_R$ is further processed in accordance with a second processing scheme in order to produce the processed sensor signal $S_B$ (block 114). Likewise, the raw sensor signal $S_R$ is also processed in accordance with additional processing schemes, if used, in order to produce additional processed sensor signals $S_n$ (block 116).

Once the weighting factors have been defined or derived, and the processed sensor signals have been produced, then the most recent processed sensor signals are retrieved (block 122). Typically, processing of the raw sensor signal will occur at a specified interval measured in terms of cardiac cycles, e.g., every cardiac cycle, every other cardiac cycle, or every five cardiac cycles. Each processed sensor signal thus retrieved is then multiplied by the appropriate weighting factor to compute corresponding multiplicand factors, $M_i$ (block 124), where $M_i = S_{Wi} \times S_i$, where the index "i" represents the letter designation of the appropriate sensor channel, A, B, ... n. The SIR signal is then generated as the sum of the various multiplicand factors $M_i$ (block 126). That is, the SIR signal is computed as $$SIR = M_A + M_B + \ldots + M_n.$$

Next, the SIR signal is provided to the rate-responsive (RR) pacing circuits (block 128). Such circuits are the conventional or other rate-responsive pacing circuits 12 shown in FIG. 1. The pacemaker is then operated pursuant to its programmed mode of operation using the SIR signal thus provided (block 130).

A determination is made as the pacemaker is operated using the most recently derived SIR signal as to whether the weighting factors should be updated (block 132). Updating of the weighting factors may occur automatically, e.g., as when the weighting factors are really weighting functions that vary with time or some other variable, or may occur by physician reprogramming. If the weighting factors are to be updated, then the new weighting factors are programmed or otherwise defined (block 120) and the method repeats as described above.

If the weighting factors are not updated, then another decision is made as to whether the method of the invention is to continue (block 134). For example, the physician may choose to program the method OFF, in which case the method would not continue, and the SIR signal would no longer be generated as a function of the separate sensor signal processing channels and the programmed weighting factors. If the method is to continue, then the raw sensor signal is again sensed (block 110) and the process repeats as described above.

As described above, it is thus seen that the invention provides a rate-responsive pacemaker utilizing an activity sensor wherein the dominance of sensed pedal impacts in determining the SIR signal is selectively controlled, as is the dominance of sensed arm motion.

As further described above, it is seen that the invention provides a rate-responsive pacemaker wherein the raw sensor signal is suitably processed to emphasize a selected aspect or aspects thereof, with the results of such processing thereafter being appropriately weighted in the formation of the SIR signal. In this manner, the sensitivity of the resulting SIR signal to various sensed events, e.g., pedal impacts and/or arm motion, is selectively controlled by appropriate weighting of the processed sensor signals.

While the invention herein disclosed has been described by means of specific embodiments and applications thereof, numerous modifications and variations could be made thereto by those skilled in the art without departing from the scope of the invention set forth in the claims.

What is claimed is:

1. An implantable rate-responsive pacemaker comprising:

pulse generator means for generating stimulation pulses on demand at a rate determined by a sensor indicated rate (SIR) signal;

an activity sensor that generates a raw sensor signal as a function of patient activity;

first sensor processing means for processing said raw sensor signal and converting said raw sensor signal to a first processed sensor signal, said first processed sensor signal being relatively sensitive to arm motion of the patient;

second sensor processing means for processing said raw sensor signal and converting said raw sensor signal to a second processed sensor signal, said second processed sensor signal being relatively sensitive to pedal impacts of the patient; and SIR signal generating means for generating said SIR signal by combining said first and second processed sensor signals in accordance with a prescribed combination function;

whereby said pulse generating means generates said stimulation pulses on demand at a rate determined by the raw sensor signal and the prescribed combination function.

2. The implantable rate-responsive pacemaker, as set forth in claim 1, further comprising telemetry means for noninvasively programming said prescribed combination function.

3. The implantable rate-responsive pacemaker, as set forth in claim 2, wherein said prescribed combination function weights said first processed sensor signal heavier than said second processed sensor signal in the formation of said SIR signal, whereby said SIR signal emphasizes arm motion of said patient relatively more than pedal impacts of said patient.

4. The implantable rate-responsive pacemaker, as set forth in claim 3, wherein said prescribed combination function weights said first processed sensor signal to be approximately 60–90% of the SIR signal, and said second processed sensor signal to be approximately 10–40% of the SIR signal.

5. The implantable rate-responsive pacemaker, as set forth in claim 2, wherein said SIR signal generating means comprises conversion means for digitizing each of said first and second processed sensor signals, multiplication means for multiplying each of said digitized processed sensor signals by an appropriate scale factor, and adding means for adding the scaled digitized processed sensor signals to produce said SIR signal, said appropriate scale factor being specified by said prescribed combination function.

6. The implantable rate-responsive pacemaker, as set forth in claim 2, wherein said prescribed combination function varies as a function of time, whereby the SIR signal is weighted by different combinations of said first and second processed sensor signals as a function of time.

7. An implantable rate-responsive pacemaker responsive to body motion of a patient, wherein determination of pacemaker rate, body motion resulting from pedal impacts may be selectively weighted differently than is body motion resulting from arm motion, said pacemaker comprising:

rate-responsive pacing means for generating stimulation pulses on demand at a rate determined by a sensor indicated rate (SIR) signal;

a body motion sensor that generates a raw sensor signal as a function of sensed body motion;

first sensor processing means for processing said raw sensor signal to generate a first processed sensor signal that is relatively more sensitive to arm motion of the patient than to pedal impacts of the patient;

second sensor processing means for processing said raw sensor signal to generate a second processed sensor signal that is relatively more sensitive to pedal impacts of the patient than to arm motion of the patient; and weighting means for combining said first and second processed sensor signals to form said SIR signal as a function of a weighting signal, said weighting signal defining how much weight is to be given each of said first and second processed sensor signals in the formation of said SIR signal.

8. The implantable rate-responsive pacemaker, as set forth in claim 7, wherein said body motion sensor comprises a piezoelectric crystal.

9. The implantable rate-responsive pacemaker, as set forth in claim 7, wherein said body motion sensor comprises a conductive element which makes and breaks electrical contact with a plurality of electrical terminals at a rate determined by the body motion.

10. The implantable rate-responsive pacemaker, as set forth in claim 7, further comprising telemetry means for allowing said weighting signal to be programmably set to a desired value.

11. An implantable rate-responsive pacemaker comprising:

a piezoelectric sensor for sensing physical motion or movement of a patient and for generating a corresponding physiological parameter indicative of a desired heart rate;

first sensor signal generating means responsive to the physiological parameter sensed by said sensor for generating a first sensor signal in accordance with a first sensor processing scheme;

second sensor signal generating means responsive to the physiological parameter sensed by said sensor for generating a second sensor signal in accordance with a second sensor processing scheme, wherein the first sensor signal generated by the first sensor processing scheme of said first sensor signal generating means is more responsive to a first type of physiological activity than is the second sensor signal generated by the second sensor processing scheme of said second sensor signal generating means, and wherein the second sensor signal is more responsive to a second type of physiological activity than is the first sensor signal;

processing means for generating a sensor indicated rate (SIR) signal as a specified combination of said first and second sensor signals;

telemetry means coupled to said processing means for allowing said specified combination of said first and second sensor signals to be programmably altered; and pacing means for providing stimulation pulses on demand at a rate determined by said SIR signal; whereby the physiological parameter sensed by said sensor controls the rate at which said pacing means provides stimulation pulses on demand as a specified combination of said first and second sensor processing schemes.

12. The implantable rate-responsive pacemaker, as set forth in claim 11, wherein the first type of physiological activity to which said first sensor signal generating means is more responsive comprises arm motion, and wherein the second type of physiological activity to which said second sensor signal generating means is more responsive comprises pedal impacts.

13. The implantable rate-responsive pacemaker, as set forth in claim 12, wherein the specified combination of said first and second sensor signals comprises 60-90% of the first sensor signal that is more responsive to arm motion, and 10-40% of the second sensor signal that is more responsive to pedal impacts.

14. An implantable rate-responsive pacemaker comprising:
  pulse generating means for generating stimulation pulses on demand at a rate determined by a sensor indicated rate (SIR) signal;
  a piezoelectric sensor that generates a raw sensor signal as a function of sensed physical motion or movement of a patient;
  sensor processing means for processing said raw sensor signal in accordance with a plurality of sensor signal processing schemes, each of said sensor signal processing schemes generating a respective plurality of processed sensor signals, with each of said processed sensor signals being more sensitive to a particular aspect of the raw sensor signal than are the other processed sensor signals;
  SIR signal generating means for combining said plurality of processed sensor signals to form said SIR signal in accordance with a prescribed function; and
  means for programmably setting said prescribed function to a desired function;
whereby said pulse generating means generates said stimulation pulses on demand at a rate determined by the raw sensor signal and the prescribed function that combines the particular aspects of said raw sensor signal to which each of the processed sensor signals is more sensitive.

15. The implantable rate-responsive pacemaker, as set forth in claim 14, wherein one of said sensor signal processing schemes is more responsive to the energy content of said raw sensor signal, which energy content tends to be more sensitive to arm motions of the patient; and another of said sensor signal processing schemes is more responsive to the filtered peak values of said raw sensor signal, which filtered peak values tend to be more sensitive to pedal impacts of the patient.

16. The implantable rate-responsive pacemaker, as set forth in claim 14, wherein said SIR signal generating means comprises conversion means for digitizing each of said processed sensor signals, multiplication means for multiplying each of said digitized processed sensor signals by an appropriate scale factor, and adding means for adding the scaled digitized processed sensor signals to produce said SIR signal, said appropriate scale factor being specified by said prescribed function.

17. A method of operating a rate-responsive pacemaker having an activity sensor that generates a raw sensor signal as a function of sensed patient activity, said method comprising the steps of:
  (a) processing the raw sensor signal in accordance with a first signal processing scheme to produce a first processed sensor signal, said first signal processing scheme being adapted to sense a first particular aspect of the raw sensor signal;
  (b) processing the raw sensor signal in accordance with a second signal processing scheme to produce a second processed sensor signal, said second signal processing scheme being adapted to sense a second particular aspect of the raw sensor signal, wherein the first sensor signal is more responsive to a first type of physiological activity than is the second sensor signal, and wherein the second sensor signal is more responsive to a second type of physiological activity than is the first sensor signal;
  (c) combining the first and second processed sensor signals in a specified combination to produce a sensor indicated rate (SIR) signal;
  (d) programmably selecting said specified combination of the first and second processed sensor signals; and
  (e) generating stimulation pulses on demand at a rate determined by said SIR signal.

18. The method, as set forth in claim 17, wherein said physiologic-related parameter comprises body motion, and wherein step (a) comprises determining the average energy content of the raw sensor signal, which average energy content is more representative of arm motion than pedal impacts.

19. The method, as set forth in claim 18, wherein step (b) comprises determining the average amplitude of the raw sensor signal above a prescribed threshold level, which average amplitude is more representative of pedal impacts than arm motion.

20. The method, as set forth in claim 17, wherein step (c) comprises weighting said first processed sensor signal more than said second processed sensor signal in producing said SIR signal, whereby said SIR signal is more sensitive to arm motion than pedal impacts.

21. The method, as set forth in claim 20, wherein step (c) comprises assigning a weighting factor to each of said first and second processed sensor signals, multiplying each of said processed sensor signals by its respective weighting factor to produce respective multiplicand factors, and adding said multiplicand factors to form said SIR signal, the weighting factor for said first processed sensor signal being greater than the weighting factor for said second processed sensor signal.

* * * * *